United States Patent [19]

Schumacher et al.

[11] Patent Number: 4,876,352

[45] Date of Patent: Oct. 24, 1989

[54] PRESSURIZED FLUORINATION OF HYDROXY ALKYL GROUPS

[75] Inventors: Doris P. Schumacher, Floraham Park; Jon E. Clark, Highland Park; Bruce L. Murphy, Glen Ridge, all of N.J.

[73] Assignee: Schering Corporation, Kenilworth, N.J.

[21] Appl. No.: 244,210

[22] Filed: Sep. 14, 1988

[51] Int. Cl.$^4$ .......................................... C07D 263/10
[52] U.S. Cl. ..................................... 548/232; 540/544; 540/612; 544/106; 544/238; 544/242; 544/358; 544/404; 546/275; 548/215; 548/229; 548/579
[58] Field of Search ............... 548/237, 239, 229, 232, 548/215; 546/275; 564/510; 260/694

[56] References Cited

U.S. PATENT DOCUMENTS

| | | | |
|---|---|---|---|
| 3,153,644 | 10/1964 | Ayer | 564/510 |
| 3,169,133 | 2/1965 | Ayer | 564/510 |
| 4,235,892 | 11/1980 | Nagabhushan et al. | |
| 4,311,857 | 1/1982 | Nagabhushan et al. | |
| 4,435,415 | 3/1984 | Bourgery et al. | 548/229 |
| 4,603,422 | 7/1986 | Fletcher | 546/275 |

FOREIGN PATENT DOCUMENTS 130633 1/1985 European Pat. Off. .

*Primary Examiner*—Donald G. Daus
*Attorney, Agent, or Firm*—John J. Maitner; Stephen I. Miller; James R. Nelson

[57] ABSTRACT

There is disclosed a high yielding process for converting a hydroxy alkyl oxazolidine compound to the corresponding fluoro derivative by reacting the hydroxy compound with α, α-difluoroalkylamine under pressure.

13 Claims, No Drawings

PRESSURIZED FLUORINATION OF HYDROXY ALKYL GROUPS

BACKGROUND OF THE INVENTION

This invention relates to an improved process for conversion of a hydroxy derivative to the corresponding fluoro compound. More particularly, this invention relates to a process for converting substituted hydroxyoxazoline compounds to the corresponding substituted fluoro derivatives. The latter compounds are useful intermediates in the preparation of D-(threo)-1-aryl-2-acylamido-3-fluoro-1-propanol compounds which are antibacterial agents.

U.S. Pat. No. 4,235,892 discloses D-(threo)-1-aryl-2-acylamido-3-fluoro-1-propanol compounds which are known in the art as broad spectrum antibacterial agents useful in the treatment of gram positive, gram negative and rickettsial infections. A preferred compound disclosed in the noted patent is D(−)-threo-1-(4-methylsulfonyl phenyl)-2-dichloroacetamido-3-fluoro-1-propanol, also known as florfenicol.

U.S. Pat. No. 4,311,857 discloses methods of preparing D-(threo)-1-aryl-2-acylamido-3-fluoro-1-propanols by reacting D-(threo)-1-aryl-2-N-protectedamino-1,3-propanediol with dialkylaminosulfur trifluoride followed by removal of the N-protecting group and then reacting the resulting D-(threo)-1-aryl-2-amino-3-fluoro-1-propanol with a lower alkanoic acid derivative.

European Patent Application 130,633 discloses oxazoline and oxazolidinone compounds useful as intermediates in preparing 1-aryl-2-amino-3-fluoro-1-propanol compounds. This patent application discloses that the primary hydroxy group of the appropriately substituted oxazoline and oxazolidinone derivatives can be replaced by fluorine utilizing various fluorinating agents; such as phosphorous fluorides, hydrofluoric acid and 2-chloro-1,1,2-trifluorotriethylamine also referred to as the Yarovenko reagent. When the latter reagent is employed as the fluorinating agent, the reaction is carried out under anhydrous conditions and in homogeneous phase, preferably in actonitrile at the boiling point temperature. The fluoro oxazoline derivative which results from the known process is then converted by a series of steps, all of which are known in the art, to the desired D-(threo)-1-aryl-2-amino-3-fluoro-1-propanol compounds.

We have now found that fluoro-substituted oxazoline compounds can be prepared in unexpectedly higher yields from hydroxy oxazoline compounds by reacting the latter compounds with α,α-difluoroalkylamine fluorinating reagents under pressure rather than by carrying out the reaction in a solvent or diluent at reflux.

SUMMARY OF THE INVENTION

This invention provides an improved process for converting hydroxy compounds to the corresponding fluoro derivative in high yields wherein the carbinol compound is reacted with an α,α-difluoroalkylamine fluorinating agent under pressure conditions. The process provides a method for preparing compounds of the formula I

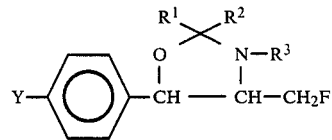

wherein Y, $R^1$, $R^2$ and $R^3$ are defined hereinafter.

DETAILED DESCRIPTION OF THE INVENTION

The process of this invention comprises treating, under pressure, an hydroxy compound

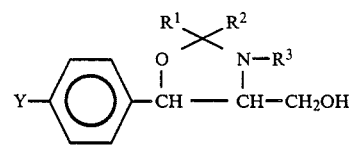

wherein
Y is hydrogen, nitro, halo, methylthio, methylsulfoxy, or methylsulfonyl;
$R^1$ is alkyl, haloalkyl, cycloalkyl, alkenyl, alkynyl, alkoxy, aralkyl, aralkenyl, aryl, aromatic heterocyclic;
$R^2$ is hydrogen, alkyl, haloalkyl, cycloalkyl, alkenyl, alkynyl, alkoxy, aralkyl, aralkenyl, aryl, aromatic heterocyclic;
$R^1$ together with $R^2$ is an oxygen atom;
$R^3$ is hydrogen; and
$R^2$ together with $R^3$ is a covalent bond, with an α,α-difluoroalkylamine fluorinating agent of the formula III

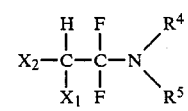

wherein
$X_1$ is chlorine or fluorine;
$X_2$ is chlorine, fluorine or trifluoromethyl;
$R^4$ and $R^5$ taken individually are alkyl, and
$R^4$ and $R^5$ taken together with the attached nitrogen atom represent the residue of heterocyclic radical containing five to seven ring atoms.

When utilized in the present specification and in the appended claims the terms listed hereinbelow, unless otherwise indicated are defined as follows:

The term "alkyl" refers to a straight saturated hydrocarbon moiety (i.e. hydrocarbons having carbon-carbon single bonds) containing from 1 to 6 carbon atoms, or a branched saturated hydrocarbon moiety of 3 to 6 carbon atoms, such as for example, methyl (i.e. —CH₃), ethyl, propyl, isopropyl, butyl, isobutyl, tert-butyl, pentyl, hexyl and the like. The term "halo" refers to fluoride, chloride, bromide or iodide. The term "haloalkyl" refers to an alkyl moiety in which one or more of the hydrogen atoms has been replaced by a halogen atom, such as, for example, chloromethyl, fluoromethyl, bromomethyl, trifluoromethyl, dichloromethyl, 2-chloro-2-fluoroethyl, 6,6,6-trichlorohexyl and the like.

The term "cycloalkyl" refers to a saturated carbocyclic ring characterized by closed rings and containing from 3 to 6 carbon atoms, such as for example, cyclopropyl, cyclobutyl, cyclopentyl, cyclohexyl, and the like.

The term "alkenyl" refers to a straight hydrocarbon moiety of two to six carbon atoms or a branched hydrocarbon moiety of three to six carbon atoms having at least one carbon-carbon double bond, such as ethenyl (i.e. $-CH=CH_2$), propenyl, 1-butenyl, 2-butenyl, isobutenyl, 1-pentenyl, 2-methyl-1-butenyl, 1-hexenyl and the like.

The term "alkynyl" refers to a straight hydrocarbon moiety of two to six carbon atoms or a branched hydrocarbon moiety of four to six carbon atoms having one carbon to carbon triple bond such as ethynyl (i.e. $-C\equiv CH$), 1-propanol, 1-butynyl, 1-pentynyl, 2-pentynyl, 1-hexynyl, 2-hexynyl, 3-hexynyl and the like.

The term "alkoxy" refers to an alkyl moiety containing from 1 to 6 carbon atoms covalently bonded to an oxygen atom, such as for example, methoxy (i.e. $-OCH3$), ethoxy, propoxy, isopropoxy, butoxy, pentoxy, hexoxy and the like.

The term "aralkyl" refers to an aryl moiety of 6 to 15 carbon atoms covalently bonded to an alkyl moiety of one to six carbon atoms such as, for example, benzyl, phenylethyl, and the like.

The term "aralkenyl" refers to an aryl moiety of six to 15 carbon atoms covalently bonded to an alkenyl moiety of two to six carbon atoms, such as, for example, 2-phenyl-1-ethenyl (cinnamyl), 4-phenyl-2-butenyl and the like.

The term "aryl" refers to a carbocyclic moiety containing at least one benzenoid-type ring, with the aryl groups preferably containing from 6 to 15 carbon atoms, for example, phenyl, naphthyl, indenyl, indanyl, and the like.

The term "aromatic heterocyclic" refers to a cyclic moiety having at least one O, S and/or N heteroatom interrupting the ring structure and having a sufficient number of unsaturated carbon to carbon double bonds, nitrogen to carbon double bonds, and the like, to provide aromatic character, with the aromatic heterocyclic groups preferably containing from 2 to 14 carbon atoms, for example, 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5- [1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, and the like.

The oxazoline compounds of formula II are prepared by known procedures; see European Patent Application No. 130,633, D. F. . Elloit, J. Chem. Soc. 1949, 589–594.

The α, α-difluoroalkylamine fluorinating agents of formula III are prepared by known procedures. U.S. Pat. No. 3,153,644 discloses the preparation of α, α-difluoroalkylamines by the reaction of α, α-difluoroalkylenes with secondary amines. The disclosure of U.S. Pat. No. 3,153,644 for the preparation α, α-difluoroalkylamine fluorinating agents utilized in the present invention is incorporated by reference.

In connection with the compound of formula III, the term "heterocyclic radical containing from 5 to 7 ring atoms" means pyrrolidino, 2-methylpyrrolidino, 2,2-dimethylpyrrolidino, and like alkylpyrrolidino groups, 4-methylpiperazino, 2,4-dimethylpiperazino, and like alkylpiperazino groups, morpholino, piperidino, 2-methylpiperidino, 3-methylpiperidino and like alkylpiperidino groups, hexamethyleneimino, homomorpholino, and the like.

Examples of fluorinating reagents of formula III are: N-(2-chloro-1,1,2-trifluoroethyl) diethylamine, N-(2-chloro-1,1,2-trifluoroethyl) dimethylamine, N-(2-chloro-1,1,2-trifluoroethyl) dipropylamine, N-(2-chloro-1,1,2-trifluoroethyl) pyrrolidine, N-(2-chloro-1,1,2-trifluoroethyl) 2-methylpyrrolidine, N-(2-chloro-1,1,2-trifluoroethyl) 4-methylpiperazine, N-(2-chloro-1,1,2-trifluoroethyl) morpholine, N-(2-chloro-1,1,2-trifluoroethyl) piperidine, N-(1,1,2,3,3,3-hexafluoropropyl) diethylamine. The preferred fluorinating agents are N-(2-chloro-1,1,2-trifluoroethyl) diethylamine and N-(1,1,2,3,3,3-hexafluoropropyl) diethylamine.

In carrying out the process of the present invention, an oxazoline compound of the formula II is reacted with an α, α-difluoroalkylamine compound of formula III in an inert solvent under pressure conditions at elevated temperatures.

The process of this invention is conducted in a closed system at elevated temperatures. The reaction is carried out by heating the reaction mixture at temperatures of about 40° C. to about 150° C., preferably at 80° C. to 125° C.

Since the reaction is carried out in a closed system, the pressure is determined by the reaction temperature and can range from slightly above atmospheric pressure to several thousand psi's. A preferred pressure range is from about 60 psi to about 100 psi. The pressure conditions may be achieved by employing a pressure reactor, such as a stainless steel reactor, teflon lined reactor, Hastelloy reactor, and the like.

The amount of α, α-difluorinated alkylamine reagent of formula III is preferably in excess over that required by stoichiometry so as to react as much as possible of the carbinol compound; however it is possible to carry out the reaction with a slight excess of the hydroxy reagent. The mole ratio of the α, α-difluorinated alkylamine reagent of formula III to the hydroxy compound is from about 0.7:1 to 5:1, more specifically 1:1 to 2:1, and preferably 1.3:1.

The process of the invention is conveniently carried out under inert conditions. This reaction can be conducted in an organic solvent which is inert to the reaction conditions. Suitable organic solvents include chlorinated hydrocarbons, such as methylene chloride, chloroform, methyl chloroform, dichloroethane; 1,1,1-trichloroethylene, chlorobenzene, 1,2-dichlorobenzene, 1,2,4-trichlorobenzene, tetrahydrofuran, acetonitrile, tert-butyl methyl ether, ethyl acetate and the like. A preferred solvent is methylene chloride.

The reaction time will be dependent upon the choice of conditions usually ranging from about 0.5 to about 24 hours. When the reaction is effectively complete, isolation of the fluorinated product may be effected by conventional procedures such as extraction, filtration, chromatography, distillation, precipitation and the like.

To eliminate or reduce any side reactions, the process may, if desired, be effected under an inert atmosphere such as nitrogen.

The present invention provides unexpectedly higher yields of fluoro-oxazoline compounds when hydroxy oxazoline compounds are reacted with α, α-difluoroalkylamine fluorinating reagents under pressure as compared to carrying out the reaction in solvent or diluent at reflux. Table I demonstrates the yield of fluoro-oxazoline compounds in accordance with the present invention as compared to the prior art process; i.e. conducting the fluorination in a solvent or diluent at reflux.

TABLE I

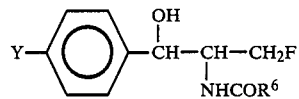

| Substrate | | | | Tempera- | Pressure | Yield |
|---|---|---|---|---|---|---|
| | $R^1$ | Y | Solvent | ture °C. | psi | (HPLC) |
| 1. | Phenyl | $CH_3SO_2$ | $CH_2Cl_2$ | 100° | 100 | 92%[a] |
| 2. | Phenyl | $CH_3SO_2$ | $CH_2Cl_2$ | Reflux | — | 14%[b] |
| 3. | Phenyl | $CH_3SO_2$ | $CH_3CN$ | 100° | 100 | 79%[a] |
| 4. | Phenyl | $CH_3SO_2$ | $CH_3CN$ | Reflux | — | 67%[b] |
| 5. | Phenyl | $CH_3SO_2$ | THF | 100° | 100 | 71%[a] |
| 6. | Phenyl | $CH_3SO_2$ | THF | Reflux | — | 21%[b] |
| 7. | $CH_3$ | $CH_3S$ | $CH_2Cl_2$ | 100° | 100 | 74%[c] |
| 8. | $CH_3$ | $CH_3S$ | $CH_2Cl_2$ | Reflux | — | 17%[c] |

[a]See Example 1
[b]See Example 4
[c]See Example 5

The fluoro-oxazoline compounds of formula can then be converted to the D-(threo)-1-aryl-2-acylamido-3-fluoro-1-propanol compounds of formula Y—⟨phenyl⟩—CH(OH)—CH(NHCOR⁶)—CH₂F Wherein $R^6$ is mono-, di-, trihalomethyl, azidomethyl or methylsulfonylmethyl, according to procedures well known in the art. For example, the fluoro-oxazoline compounds can be reacted with acid, preferably inorganic acids, in aqueous medium or in water/organic diluent mixtures to afford the D-(threo)-1-aryl-2-amino-3-fluoro-1-propanol. The latter compound is then reacted with a lower alkanoic acid, lower haloalkanoic acid, or derivatives thereof, such as an acid chloride or anhydride, in the presence of base.

The following examples describe in detail the invention. It will be apparent to those skilled in the art that modification, both of materials and methods, may be practiced without departing from the purpose and intent of this disclosure.

Preparation of Fluorinating Agents

1. N-(2-Chloro-1,1,2-trifluoroethyl)diethylamine.

Chlorotrifluoroethylene (454 g; 3.91 mole) is bubbled into diethylamine (350 g; 4.8 mole) over about 6 hours while the temperature is maintained at 30°–45° C. by use of an ice bath. The mixture is stirred overnight at room temperature and then distilled in vacuo to give 415 g (2.2M) of N-(2-chloro-1,1,2-trifluoroethyl)-diethylamine.

2. N-(1,1,2,3,3,3-Hexafluoropropyl)diethylamine.

Hexafluoropropylene (260 g; 1.73 mole) is bubbled into a solution of 287 ml (200 g; 2.74 mole) of diethylamine and 400 mL of methylene chloride over approximately 2 hours, keeping an internal temperature of about 10° with use of an ice bath. The reaction mixture is then stirred at room temperature for 18 hours. Low boiling compounds are removed by distillation at 70–80 mm and the product is distilled at 27°–32° C. and 8–10 mm, producing 238 ml (293 g; 1.31 mole) of N-(1,1,2,3,3,3-hexafluoropropyl)diethylamine.

EXAMPLE 1

D-THREO-2-PHENYL-4-FLUOROMETHYL-5-(4-METHYLSULFONYLPHENYL)-2-OXAZOLINE (a) To 0.25 g (0.754 m mole) of D-threo-2-phenyl-4-hydroxymethyl-5-(4-methylsulfonylphenyl)-2-oxazoline suspended in 2.5 ml. of dry methylene chloride at room temperature and under nitrogen, was added 0.18 ml. (0.22 g., 0.980 m mole) of N-(1,1,2,3,3,3-hexafluoropropyl) diethylamine. The mixture was added to a Teflon bomb and the bomb was heated in an oil bath at 100° C. for 3 hours. After cooling to 0° C., the reactor was opened and the reaction mixture extracted with ethyl acetate and washed with water and brine. A yield of 92% of D-threo-2-phenyl-4-fluoromethyl-5-(4-methylsulfonylphenyl)-2-oxazoline was obtained when compared to an external standard using HPLC.

(b) The procedure of (a) was repeated except that the methylene chloride solvent was replaced by acetonitrile, a yield of 79% of D-threo-2-phenyl-(4-fluoromethyl) -5-(4-methylsulfonylphenyl)-2-oxazoline was obtained when compared to an external standard using HPLC.

(c) The procedure of (a) was repeated except that the methylene chloride solvent was replaced by tetrahydrofuran, a yield of 71% of D-threo-2-phenyl-4-fluoromethyl-5-(4-methylsulfonylphenyl)-2-oxazoline was obtained when compared to an external standard using HPLC.

(d) The procedure of (a) was repeated except that the reactor was heated to a temperature of 80° C, a yield of 91% of D-threo-2-phenyl-4-fluoromethyl-5-(4-methylsulfonylphenyl)-2-oxazoline was obtained when compared to an external standard.

(e) The procedure of (a) was repeated except that the reactor was heated to a temperature of 125° C, a yield of 92% of D-threo-2-phenyl-4-fluoromethyl-5-(4-methylsulfonyl)-2-oxazoline was obtained when compared to an external standard.

EXAMPLE 2

D-(THREO)-2-PHENYL-4-FLUOROMETHYL-5-(4-METHYLSULFONYL PHENYL)-2-OXAZOLINE

To a slurry of 0.5 g (1.67 m moles) of D-threo-2-phenyl-4-hydroxymethyl-5-(4-methylsulfonylphenyl)-2-oxazoline in 10 ml. of methylene chloride was added 0.39 ml. (0.48 g., 2.17 m moles) of N-(2-chloro-1,1,2-trifluoroethyl) diethylamine. The mixture was added to a Teflon bomb and the reactor was heated in an oil bath at 110° C for 45 minutes. After cooling to 0° C, the bomb was opened and the reaction mixture was extracted with ethyl acetate and washed with water and brine. A yield of 92% of D-(threo)-2-phenyl-4-fluoromethyl)-5-4-methylsulfonyl phenyl-2-oxazoline was obtained when compared to an external standard.

EXAMPLE 3

D-(THREO)-2-PHENYL-4-FLUOROMETHYL-5-(4-METHYL-THIOPHENYL) -2-OXAZOLINE (a) A suspension of 0.25 g. (0.84 m mole) of D-(threo)-2-phenyl-4-hydroxymethyl-5-(4-methylthiophenyl)-2-oxazoline in 2.5 ml. of dry methylene chloride was placed in a Teflon bomb. While maintaining the reaction slurry under nitrogen, 0.23 ml (0.28 g., 1.24 m mole)

of N-(1,1,2,3,3,3-hexafluoropropyl) diethylamine was added to the mixture. The bomb was closed and heated in an oil bath at 100° C for 3 hours. After cooling to about 0° C, the reactor was opened and the reaction mixture diluted with ethyl acetate. The solution was washed twice with water and the aqueous washes were back extracted once with ethyl acetate. The combined organic layers were washed once with brine and concentrated. The residue was dissolved in methylene chloride, filtered to remove any salt and concentrated to afford a yield of 86% of D-(threo)-2-phenyl-4-fluoromethyl-5-(4-methylthiophenyl)-2-oxazoline when compared to an external standard.

(b) The procedure of (a) was repeated except that the reaction mixture was heated at reflux for 3 hours. A yield of 13% of D-(threo)-2-phenyl-4-fluoromethyl-5-(4-methylthiophenyl)-2-oxazoline was obtained when compared to an external standard using HPLC.

EXAMPLE 4

D-(THREO)-2-PHENYL-4-FLUOROMETHYL-5-(4-METHYLSULFONYLPHENYL)-2-OXAZOLINE (a) To 0.25 g (0.754 m mole) of D-(threo)-2-phenyl-4-fluoromethyl-5-(4-methylsulfonylphenyl)-2-oxazoline suspended in 2.5 ml. of dry methylene chloride at room temperature and under nitrogen, was added 0.18 ml. (0.22 g., 0.980 m mole) of N-(1,1,2,3,3,3-hexafluoropropyl) diethylamine. The reaction was heated at reflux for 2 hours. A yield of 14% of D-(threo)-2-phenyl-4-fluoromethyl-5-(4-methylsulfonylphenyl)-2-oxazoline was obtained when compared to an external standard using HPLC.

(b) The process was repeated except that the methylene chloride solvent was replaced by acetonitrile, a yield of 67% of D-(threo)-2-phenyl-4-fluoromethyl-5-(4-methylsulfonylphenyl)-2-oxazoline was obtained when compared to an external standard using HPLC.

(c) The process was repeated except that the methylene chloride solvent was replaced by tetrahydrofuran, a yield of 21% of D-(threo)-2-phenyl-4-fluoromethyl-5-(4-methylsulfonylphenyl)-2-oxazolin was obtained when compared to an external standard using HPLC.

EXAMPLE 5

D-(THREO)-2-METHYL-4-FLUOROMETHYL-5-(4-METHYLTHIOPHENYL)-2-OXAZOLINE (a) To 0.25 g (1.05 m mole) of D-(threo)-2-methyl-4-hydroxymethyl-5-(4-methylthiophenyl)-2-oxazoline suspended in 2.5 ml. of dry methylene chloride at room temperature and under nitrogen, was added 0.38 ml. (0.47 g., 2.11 m mole) of N-(1,1,2,3,3,3-hexafluoropropyl) diethylamine. The mixture was added to a Teflon bomb and the bomb was heated in an oil bath at 100° C for 2 hours. After cooling to 0° C, the bomb was opened and the reaction mixture extracted with ethyl acetate and washed with water and brine. A yield of 74% of D-(threo)-2-methyl-4-fluoromethyl-5-(4-methylthiophenyl)-2-oxazoline was obtained when compared to an external standard using HPLC.

(b) The procedure (a) was repeated except that the reaction mixture was heated at reflux for 2 hours. A yield of 17% of D-(threo)-2-methyl-4-fluoromethyl-5-(4-methylthiophenyl)-2-oxazoline was obtained when compared to an external standard using HPLC

EXAMPLE 6

5-(4-METHYLTHIOPHENYL)-4-FLUOROMETHYLOXAZOLIDIN-2-ONE

To a solution of 250 mg (1.0 mmole) of 5-(4-methylthiophenyl)-4-hydroxymethyl-oxazolidin-2-one in 30 ml of methylene chloride was added 0.21 ml (1.3 moles) of N-(2-chloro-1,1,2-trifluoroethyl)-diethylamine. The reaction mixture was heated in a teflon bomb at 110° C for 1.5 hours. The reaction mixture was cooled and diluted with ethyl acetate. The organic layer was washed twice with water, dried and concentrated. Chromatography on silica gel afforded 150 mg (0.62 mmole), 62% of 5-(4-methylthiophenyl)-4-fluoromethyl-oxazolidin-2-one.

EXAMPLE 7

D-(THREO)-1-(4-METHYLSULFONYLPHENYL)-2-DICHLOROACETAMIDO-3-FLUORO-1-PROPANOL

To 1.00 g (2.96 mmole) of D-(threo)-2-dichloromethyl-4-hydroxymethyl-5-(4-methylsulfonylphenyl)-2-oxazoline in 10 ml of dry methylene chloride at room temperature was added 0.70 ml (0.86 g, 3.84 mmole) of N-(1,1,2,3,3,3-hexafluoropropyl)diethylamine. The mixture was heated in a Teflon bomb at 100° C for 3 hours. After cooling to 0° C, the bomb was opened and the contents warmed to room temperature. To the reaction mixture was added 0.30 ml of 12N HCl and the solution was stirred at room temperature for 1 hour. About 0.5 ml of 28% ammonium hydroxide was added to adjust the pH to 10. Removal of the solvent under vacuum afforded an HPLC purity corrected yield of 1.01 g (95%) of D-(threo)-1-(4-methylsulfonylphenyl)-2-dichloroacetamido-3-fluoro-1-propanol.

EXAMPLE 8

D-(THREO)-1-(4-METHYLSULFONYLPHENYL)-2-DICHLOROACETAMIDO-3-FLUORO-1-PROPANOL a) To 500 ml of 12N HCl heated at about 100° C was added 46.5 g (0.138 moles) of D-threo-2-phenyl-4-fluoromethyl-5-(4-methylsulfonylphenyl)-2-oxazoline in 500 ml of methylene chloride over 0.5 hour allowing the methylene chloride to distill from the reaction vessel. After removing the methylene chloride, the reaction mixture was heated at 100° C for 18 hours. After cooling to room temperature, the solution was extracted two times with ethyl acetate and the combined organic layers were back extracted once with N HCl. The combined acidic aqueous solutions were concentrated and the residual water removed by azeotropic distillation with isopropanol. The residual solid was triturated with acetonitrile (about 150 ml) and cooled to 5° C. The solids were collected by filtration, washed with cold acetonitrile, dried under vacuum at 15° C to afford 62 g (HPLC purity 53%; 89% of theory) of D-(threo)-1-(4-methylsulfonylphenyl)-2-amino-3-fluoro-1-propanol hydrochloride.

b) To a solution of 9.95g (30.2 mmole) of D-(threo)-1-(4-methylsulfonylphenyl)-2-amino-3-fluoro-1-propanol hydrochloride in 100 ml of methanol was added 4.2 ml (30.2 mmole, 3.05 g) of triethylamine and 15.6 ml (21.6g, 151 mmole) of methyl dichloroacetate. The reaction mixture was stirred at room temperature for 24 hours and concentrated to less than one-fourth volume. Water was added and the resulting precipitate was filtered and dried to afford 8.62g of D-(threo)-1-(4-methylsulfonylphenyl)-2-dichloroacetamido-3-fluoro-1-propanol. Recrystallization from isopropanol afforded 6.61g of product.

EXAMPLE 9

Repeating the procedure detailed in Example 1(a) and utilizing the appropriate hydroxy-oxazoline compound of formula II affords the following compounds in yields isolated by column chromatography:

1. D-(threo)-2-(4-dimethylaminophenyl)-4-fluoromethyl-5-(4-methylsulfonylphenyl)-2-oxazoline - 93% yield.
2. D-(threo)-2-(3-methyl-2-pyridinyl)-4-fluoromethyl-5-(4-methylsulfonylphenyl)-2-oxazoline - 63% yield.
3. D-(threo)-2-(4-nitrophenyl)-4-fluoromethyl-5-(4-methylsulfonylphenyl)-2-oxazoline - 92% yield.
4. D-(threo)-2-(4-methoxyphenyl)-4-fluoromethyl-5-(4-methylsulfonylphenyl)-2-oxazoline - 88% yield.
5. D-(threo)-2-(4-methoxy cinnamyl)-4-fluoromethyl-5-(4-methylsulfonylphenyl)-2-oxazoline - 67% yield.

What is claimed:

1. A process for preparing compounds of the formula

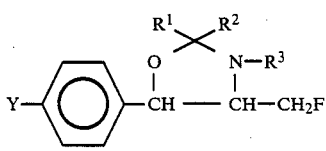

wherein

Y is hydrogen, nitro, methylthio, methylsulfoxy, or methylsulfonyl;

$R^1$ is alkyl, haloalkyl, cycloalkyl, alkenyl, alkynyl, alkoxy, aralkyl, aralkenyl, aryl, aromatic heterocyclic;

$R^2$ is hydrogen, alkyl, haloalkyl, cycloalkyl, alkenyl, alkynyl, alkoxy, aralkyl, aralkenyl, aryl, aromatic heterocyclic;

$R^1$ together with $R^2$ is an oxygen atom;

$R^3$ is hydrogen; and $R^2$ together with $R^3$ is a covalent bond, with an α, α-difluoroalkylamine fluorinating agent of the formula III which comprises treating under pressure a compound of the formula

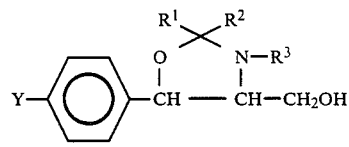

wherein

Y and R are defined hereinabove, with an α, α-difluoroalkylamine fluorinating agent of the formula III

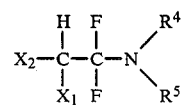

wherein $X_1$ is chlorine or fluorine, $X_2$ is chlorine, fluorine or trifluoromethyl $R^4$ and $R^5$ taken individually are loweralkyl, and $R^4$ and $R^5$ taken together with the attached nitrogen atom represent the residue of a heterocyclic radical contain five to seven ring atoms.

2. The process of claim 1 wherein the reaction is carried out at a pressure of from about 60 psi to about 100 psi.

3. The process of claim 2 wherein the reaction is carried out in an inert organic solvent.

4. The process of claim 3 wherein the inert organic solvent is selected from the group consisting of methylene chloride, chloroform, methylchloroform, 1,1,1-trichloroethylene, dichloroethane, chlorobenzene, 1,2-dichlorobenzene, 1,2,4-trichlorobenzene, ethyl acetate, tetrahydrofuran, acetonitrile, and dimethylformamide.

5. The process of claim 4 wherein the inert organic solvent is methylene chloride.

6. The process of claim 1 wherein the reaction is carried out at a temperature of about 40° C to about 150° C.

7. The process of claim 5 wherein the reaction is carried at a temperature of from 85° C to 125° C.

8. The process of claim 1 wherein the α, α-difluoroalkylamine compound of formula III is N-(2-chloro-1,1,2-trifluoroethyl) diethylamine.

9. The process of claim 1 wherein the α, α-difluoroalkylamine compound of formula III is (N-(1,1,2,3,3,3-hexafluoropropyl) diethylamine.

10. The process of claim 1 wherein the oxazoline compound of formula II is 2-phenyl-4-hydroxymethyl-5-(4-methylsulfonylphenyl)-2-oxazoline.

11. The process of claim 1 wherein the oxazoline compound of formula II is 2-phenyl-4-hydroxymethyl-5-(4-methylthiophenyl)-2-oxazoline.

12. The process of claim 1 wherein the oxazoline compound of formula II is 2-phenyl-4-hydroxymethyl-5-(4-methylsulfoxyphenyl)-2-oxazoline.

13. The process of claim 1 wherein the oxazoline compound of formula II is 2-dichloromethyl-4-hydroxymethyl-5-(4-methylsulfonylphenyl)-2-oxazoline.

* * * * *